United States Patent [19]

Korkis

[11] 3,957,970
[45] May 18, 1976

[54] SHAMPOO CONTAINING AN ESTER OF POLYETHYLENE GLYCOL, UREA OR THIOUREA AND A POLYSILOXANE

[75] Inventor: George N. Korkis, Paramus, N.J.

[73] Assignee: American Cyanamid Company, Stamford, Conn.

[22] Filed: June 6, 1974

[21] Appl. No.: 476,977

[52] U.S. Cl............................ 424/70; 252/DIG. 1; 252/DIG. 2; 252/DIG. 7; 252/DIG. 13; 252/118; 252/153; 252/548; 252/550; 424/358; 424/362; 424/365
[51] Int. Cl.$^2$........................................... A61K 7/06
[58] Field of Search................... 424/70, DIG. 2, 78; 252/DIG. 1, DIG. 2, DIG. 13, DIG. 7, 118, 153, 548, 550

[56] References Cited
UNITED STATES PATENTS 3,824,303   7/1974   Lanzet et al...................... 424/73 X

OTHER PUBLICATIONS

Jellinek, Formulation and Function of Cosmetics, Wiley–Interscience, New York, (1970), pp. 250–255, 464 and 500.

Primary Examiner—Sam Rosen
Assistant Examiner—Vera C. Clarke
Attorney, Agent, or Firm—Charles J. Fickey

[57] ABSTRACT

An improved shampoo composition is provided which comprises a synthetic detergent or a mixture comprising 50 to 60 percent by weight of a soap and 40 to 60 percent by weight of a synthetic detergent, the improvement which comprises the addition of a composition consisting essentially of (a) from about 0.1 to 5 percent by weight of either a mono or diester of polyethylene glycol having a molecular weight of from about 400 to 6000; (b) from about 0.1 to 5 percent by weight of urea or thiourea; and, (c) from about 1 to 4 percent by weight of a liquid polyether modified polysiloxane.

5 Claims, No Drawings

IMPROVED SHAMPOO CONTAINING AN ESTER OF POLYETHYLENE GLYCOL, UREA OR THIOUREA AND A POLYSILOXANE

Generally stated, the subject matter of the present invention relates to an improved shampoo composition. More particularly, the invention relates to a shampoo composition comprising a system which serves to overcome those side effects inherent in the use of shampoos.

BACKGROUND OF THE INVENTION

Shampoos have been defined as surfactant preparations in either liquid, solid or powder form which when used under specific conditions will remove surface grease, dirt and skin debris from the hair shaft and scalp without adversely affecting the hair, scalp and health of the user. In addition, a shampoo should not only be a detergent composition, but a cosmetic as well, in that it should impart lustre, beauty and manageability to the hair. Therefore, not only must the shampoo provide cleaning, but it must also serve a cosmetic function as well.

Heretofore most attempts to achieve this cosmetic objective have met with limited success; namely, the hair after shampooing is frequently tangled, as well as lacking smoothness and manageability. This has prompted the evolution of the so called creme rinses which are applied after shampooing to impart lustre and manageability to the hair.

The present invention represents the culmination of a long series of investigations conducted largely by the inventor directed to finding a shampoo composition which serves to materially overcome those disadvantages inherent in the use of shampoos.

Accordingly, it is a primary object of the present invention to provide an improved shampoo composition which avoids the inherent problems of shampoos.

Another object of the invention is to provide a shampoo composition which avoids that tangling effect most commonly demonstrated in wet hair by the criteria of effective wet combing.

Still another object of the invention is to provide a shampoo composition which imparts a smoothness to both wet and dry hair.

Yet another object of the invention is to provide a shampoo composition which materially reduces the unmanageability so frequently encountered in dry hair after shampooing.

Additional objects and advantages will be set forth in part in the description which follows, and in part will be obvious from the description or may be learned by practice of the invention, the objects and advantages being realized and attained by means of the compositions, processes and improvements particularly pointed out in the appended claims.

THE INVENTION

To achieve the foregoing objects and in accordance with its purpose, this invention as embodied and broadly described, provides an improved shampoo composition comprising a synthetic detergent or a mixture comprising 50 to 60 percent by weight of a soap and 40 to 60 percent by weight of a synthetic detergent, the improvement which comprises the addition of a composition consisting essentially of (a) from about 0.1 to 5 percent by weight of either a mono or diester of polyethylene glycol having a molecular weight of from about 400 to 6000; (b) from about 0.1 to 5 percent by weight of urea or thiourea; and, (c) from about 1 to 4 percent by weight of a liquid polyether modified polysiloxane.

It is to be understood that both the foregoing general description and the following detailed description are exemplary and explanatory but are not restrictive of the invention.

As indicated, the shampoo of the present invention can consist of a mixture of soaps and synthetic detergents and depending on the end use of the shampoo, that is whether the shampoo is being formulated for use on dry, oily or normal hair, varying amounts of soap and synthetic detergents are used. The shampoo may be formulated with conditioners, solvents, preservatives, thickeners, fragrances, water and the like.

As herein employed, the soap component of the shampoo can be any of those soaps usually employed in shampoo formulations. Illustrative of such soaps are those products of triethanolamine with fatty acids, such as oleic acid, tall oil, coconut fatty acid, lauric acid, lauric-myristic acids and the like. A preferred combination of soaps includes tall oil, coconut fatty acid and triethanolamine.

The synthetic detergent can employ many surfactants or combination of surfactants such as the anionic, nonionic or amphoteric surfactants.

Typically useful anionic surfactants include sodium lauryl sulfate, sodium lauryl ether sulfate, triethanolamine lauryl sulfate and triethanolamine oleyl coco sarcosinate.

Illustrative of the nonionic surfactants are the fatty acids alkanolamides such as capric diethanolamide, lauricmyristic diethanolamide and fatty acid alkanolamides such as those marketed by Stephan Chemical Company as Ninol P-621 and Ninon AA-62. The amphoteric surfactants include coco amido betaines such as Tegobetain C, Goldschmidt Chemical Division, Wilson Pharmaceutical Chemical Corp., coco betaine such as Chemadene NA-30, Richardson Co., coco amino betaines, such as Lonzaine 12 C, Lonza, Inc., dicarboxylic coconut derivatives such as Miranol $C_2$M-SF, Miranol Chemical Company, decylamino betaine and N-lauryl myristyl beta aminopropionic acid, such as Deriphat 170 C, General Mills Chemicals Inc.

The inventive concept herein disclosed and claimed resides in a three component composition comprising an ester of polyethylene glycol, urea or thiourea and a liquid polyether modified polysiloxane. The mono and diesters of polyethylene glycol vary in molecular weight from about 400 to 6000 and an illustrative ester would be the mono or distearate. Typical esters are polyethylene glycol 400 distearate, polyethylene glycol 6000 distearate and polyethylene glycol 6000 mono and distearate. Polyethylene glycol 6000 distearate is preferred. The ester is present in a concentration of from about 0.1 to 5 percent by weight, based on the total weight of the shampoo. A preferred concentration is from 1 to 2 percent by weight.

The urea of thiourea is employed at a concentration of from about 0.1 to 5 percent by weight, based on the total weight of the shampoo composition. The preferred concentration is 1 to 2 percent.

The liquid polyether modified polysiloxane employed in the present invention is usually referred to as a solubilized silicone which is a copolymer of an alkylene glycol such as ethylene glycol and dimethyl siloxane.

Illustrative of the liquid polyether modified polysiloxanes are Silicone L-530, Union Carbide, Silicone 474A fluid, Dow Corning and Silicone SF-1066, General Electric among others.

The average empirical formula of these compounds may be represented as follows:

G.E.S.F. 1066 Type Structure

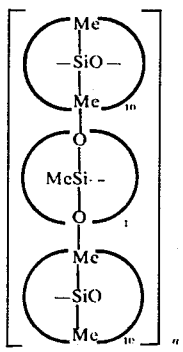

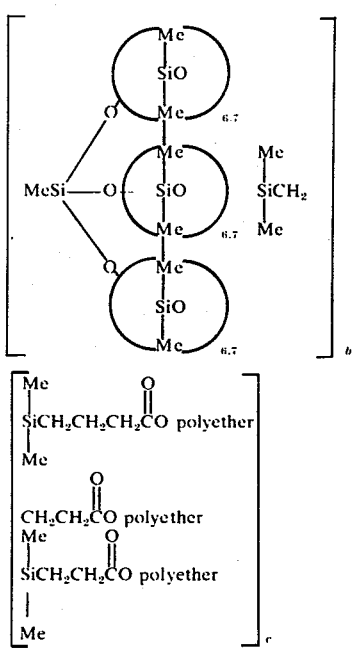

wherein $a+b$ equals 1 and $a$ or $b$ may be zero and $c$ is equal to 1, or (The polyether moiety of the above empirical formula of G.E.S.F. 1066 has an average molecular weight of 1800 and is comprised of ethylene oxide and propylene oxide in a molar ratio of 1:1).

G.E.S.F. 1066 is chemically an equilibrated carboxyalkyl containing dimethyl silicone fluid esterified with a monohydroxyl polyether. The polysiloxane is present in the composition at a concentration of from about 1 to 4 percent by weight, based on the weight of the total composition, the preferred concentration is 1 to 2 percent.

The following examples are provided for illustrative purposes and may include particular features of the invention. However, the examples should not be construed as limiting the invention, many variations of which are possible without departing from the spirit or scope thereof.

EXAMPLE I

DRY HAIR FORMULATION

The following composition was prepared by placing the soap phase components in a suitable container provided with mixing means and heating same to 50°C. The synthetic detergent phase is then added to the container followed by the remaining ingredients.

| Component | % by Weight |
|---|---|
| Propylene glycol (solvent) | 8.0 |
| Tall oil | 7.0 |
| Coconut fatty acid | 5.0 |
| Triethanolamine | 6.72 |
| Triethanolamine lauryl sulfate (40%) | 20.5 |
| Coco amido alkyl betaine (30%) | 5.0 |
| Triethanolamine oleyl sacrosinate (30%) | 3.0 |
| Alkanolamide (Ninol P-621), (100%) | 3.0 |
| PEG 6000 Distearate (non-ionic conditioner) | 1.0 |
| Urea | 2.0 |
| Copolymer of ethylene glycol and dimethyl siloxane* | 1.0 |
| Tetra sodium salt of ethylenediamine tetraacetic acid | 1.0 |
| Preservative | 0.05 |
| Viscogel** (thickener), (3.3%) | 5.0 |
| Fragrance | 0.5 |
| Deionized water | 31.23 |

*Silicone L-530 Union Carbide
**Methyl cellulose dispersed in water with the aid of TEA lauryl sulfate (1.47%).

EXAMPLE II

NORMAL HAIR FORMULATION

The following composition was prepared in the same manner as Example I.

| Component | % by Weight |
|---|---|
| Propylene glycol | 8.0 |
| Tall oil | 7.0 |
| Coconut fatty acid | 5.0 |
| Triethanolamine | 6.72 |
| Triethanolamine lauryl sulfate (40%) | 9.4 |
| Sodium lauryl sulfate | 10.0 |
| Coco amido alkyl betaine (30%) | 5.0 |
| PEG 6000 Distearate | 1.0 |
| Urea | 2.0 |
| Copolymer of ethylene glycol and dimethyl siloxane* | 1.0 |
| Tetra sodium salt of ethylenediamine tetraacetic acid | 1.0 |
| Preservative | 0.05 |
| Alkanolamide (Ninol P-621), (100%) | 4.0 |
| Viscogel* (thickener), (3.3%) | 2.0 |
| Fragrance | 0.5 |
| Deionized water | 37.33 |

*Silicone L-530 Union Carbide
**Methyl cellulose dispersed in water with the aid of TEA lauryl sulfate (1.47%).

EXAMPLE III

OILY HAIR FORMULATION

The following composition was prepared in the same manner as Example I.

| Component | % by Weight |
|---|---|
| Polypropylene glycol | 8.0 |
| Tall oil | 7.0 |
| Coconut fatty acid | 5.0 |
| Triethanolamine | 6.72 |
| Sodium lauryl sulfate | 32.4 |
| Alkanolamide (Ninol P-621), (100%) | 5.0 |
| PEG 6000 Distearate | 1.0 |

-continued

| Component | % by Weight |
|---|---|
| Urea | 2.0 |
| Copolymer of ethylene glycol and dimethyl siloxane* | 1.0 |
| Tetra sodium salt of ethylenediamine tetraacetic acid | 1.0 |
| Preservative | 0.05 |
| Viscogel** (thickener) (3.3%) | 2.0 |
| Fragrance | 0.5 |
| Deionized water | 28.33 |

*Silicone L-530 Union Carbide
**Methyl cellulose dispersed in water with the aid of TEA lauryl sulfate (1.47%).

EXAMPLE IV

EVALUATION OF COMPOSITIONS

A salon evaluation was conducted by licensed hair dressers, trained in the scientific evaluation of hair care products. Standard half-head techniques were used to evaluate the compositions of the present invention versus a competitive, commercially successful shampoo composition. Wet hair and dry hair evaluations were made with the results shown in the accompanying table. In the table "D", "N" and "O" refer to dry, normal and oily hair, respectively.

TABLE

| | | | Compositions of Examples I – III | Competitive Product | Equal | No. of Subjects |
|---|---|---|---|---|---|---|
| "D" | | | | | | |
| | Wet | (Tangle Control | 71.4% | 0.0% | 28.6% | 14 |
| | | (Smoothness | 64.3 | 14.3 | 21.4 | 14 |
| | Dry | (Tangle Control | 64.3 | 0.0 | 35.7 | 14 |
| | | (Static Control | 64.3 | 7.1 | 28.6 | 14 |
| | | (Smoothness | 78.5 | 7.1 | 14.4 | 14 |
| "N" | | | | | | |
| | Wet | (Tangle Control | 70.0% | 0.0% | 30.0% | 10 |
| | | (Smoothness | 70.0 | 20.0 | 10.0 | 10 |
| | Dry | (Tangle Control | 30.0 | 10.0 | 60.0 | 10 |
| | | (Static Control | 70.0 | 10.0 | 20.0 | 10 |
| | | (Smoothness | 20.0 | 20.0 | 60.0 | 10 |
| "O" | | | | | | |
| | Wet | (Tangle Control | 100.0% | 0.0% | 0.0% | 3 |
| | | (Smoothness | 100.0 | 0.0 | 0.0 | 3 |
| | Dry | (Tangle Control | 33.0 | 0.0 | 67.0 | 3 |
| | | (Static Control | 33.0 | 0.0 | 67.0 | 3 |
| | | (Smoothness | 66.0 | 34.0 | 0.0 | 3 |

What is claimed is:

1. In a shampoo composition comprising an aqueous carrier, a mixture comprising 50 to 60 percent by weight of a soap and 40 to 60 percent by weight of a synthetic detergent, the improvement which comprises the addition thereto of a composition, based upon the total weight of shampoo composition, consisting essentially of, (a) from about 0.1 to 5 percent by weight of either a mono or diester of polyethylene glycol having a molecular weight of from about 400 to 6000; (b) from about 0.1 to 5 percent by weight of urea or thiourea; and, (c) from about 1 to 4 percent by weight of a liquid copolymer of an alkylene glycol and dimethyl siloxane.

2. The composition according to claim 1 wherein the ester of polyethylene glycol is polyethylene glycol 6000 distearate.

3. The composition according to claim 2 wherein the concentration of (a) is from 1 to 2 percent by weight.

4. The composition according to claim 1 wherein (b) is urea in a concentration of from 1 to 2 percent by weight.

5. The composition according to claim 1 wherein (b) is thiourea in a concentration of from 1 to 2 percent by weight.

* * * * *